United States Patent
Sheehan

(10) Patent No.: US 7,547,555 B2
(45) Date of Patent: Jun. 16, 2009

(54) USE OF TEMPERATURE AND FLOW PROFILES IN GRADIENT ELUTION BASED ANALYTICAL PROCESS

(75) Inventor: Terry L. Sheehan, Walnut Creek, CA (US)

(73) Assignee: Varian, Inc., Palo Alto, CA (US)

( * ) Notice: Subject to any disclaimer, the term of this patent is extended or adjusted under 35 U.S.C. 154(b) by 867 days.

(21) Appl. No.: 10/533,346

(22) PCT Filed: Oct. 29, 2003

(86) PCT No.: PCT/US03/34442

§ 371 (c)(1),
(2), (4) Date: Apr. 29, 2005

(87) PCT Pub. No.: WO2004/042384

PCT Pub. Date: May 21, 2004

(65) Prior Publication Data

US 2007/0048187 A1    Mar. 1, 2007

Related U.S. Application Data

(60) Provisional application No. 60/422,465, filed on Oct. 30, 2002.

(51) Int. Cl.
*G01N 24/00* (2006.01)

(52) U.S. Cl. ..................................... 436/173; 436/147
(58) Field of Classification Search ...................... None
See application file for complete search history.

(56) References Cited

U.S. PATENT DOCUMENTS

2002/0023878 A1 *  2/2002  Collins et al. ............... 210/635
2002/0039747 A1 *  4/2002  Lubman et al. .............. 435/7.1

* cited by examiner

*Primary Examiner*—Yelena G Gakh
(74) *Attorney, Agent, or Firm*—Bella Fishman; David P. Gloekler

(57) ABSTRACT

A method and apparatus are provided for optimizing a liquid chromatography/mass spectrometry system for gradient elution. A temperature profile is determined according to which a gas is flowed into an atmospheric pressure ionization interface for vaporizing a matrix flowed into the interface from a liquid chromatography column. A flow profile is determined according to which the gas is flowed into the interface for preventing entry of the matrix into the mass spectrometer when the matrix does not include an analyte for which detection is desired. The determination of the temperature and flow profiles is based on the characteristics of the matrix as it eludes from column into the interface. A heat control device and a flow control device can be provided for implementing the temperature profile and flow profile, respectively. The heating control device and flow control device can be programmed or controlled by software.

13 Claims, 2 Drawing Sheets

USE OF TEMPERATURE AND FLOW PROFILES IN GRADIENT ELUTION BASED ANALYTICAL PROCESS

RELATED APPLICATION

This application claims the benefit of U.S. Provisional Patent Application Ser. No. 60/422,465, filed Oct. 30, 2002, the disclosure of which is incorporated herein by reference in its entirety.

FIELD OF THE INVENTION

The subject matter disclosed herein generally relates to analytical separation and detection techniques based on liquid chromatography and mass spectrometry, and particularly techniques in which a gradient elution is implemented. More specifically, the subject matter disclosed herein relates to optimization of such techniques by controlling parameters of a drying gas interacting with chromatographic eluent.

BACKGROUND OF THE INVENTION

Liquid chromatography (LC) is a popular technique for performing an analytical separation of a sample into constituent components, i.e., the analytes of interest to a researcher. As readily known by persons skilled in the art, during the course of a chromatographic separation, the sample is transported in a mobile phase, which is a liquid in LC techniques. The mobile phase is forced through a stationary phase that is immiscible relative to the mobile phase. Typically, the stationary phase is supported in a column or cartridge through which the sample and mobile phase flow. The respective compositions of the mobile phase and stationary phase are selected to cause the analytes of the sample to become distributed between the mobile phase and stationary phase to varying degrees dependent on the nature of the respective analytes. Analytes that are strongly retained by the stationary phase travel slowly with the mobile phase, while analytes that are weakly retained by the stationary phase travel more rapidly. As a result, analytes of differing compositions become separated from each other as the mobile phase flows through the column. In this manner, the analytes are in effect sorted sequentially as the eluent flows out from the column, thereby facilitating their analysis by a suitable analytical instrument.

One particularly useful instrument for analyzing the separated components of the sample is a mass spectrometer. Several different types of mass spectrometers are commercially available and well known to persons skilled in the art. The advent of mass spectrometers that utilize an atmospheric pressure ionization (API) interface between the sample input and the input into the mass analyzing and detection portions of the mass spectrometer, such as an electrospray ionization (ESI) source or an atmospheric pressure chemical ionization (APCI) source, has enabled the eluent from an LC column to be fluidly connected to the mass spectrometer. The resulting system is commonly termed a liquid chromatography/mass spectrometry (LC/MS) system.

Generally, the API interface of a mass spectrometer converts the column eluent, i.e., an analyte/mobile phase matrix, into droplets that must be vaporized or desolvated so that the analytes can be ionized in preparation for processing in the evacuated regions of the mass spectrometer. Typically, a stream of an inert drying gas such as diatomic nitrogen is flowed into the API interface to enhance evaporation of the droplets. Often, a separate stream of nebulizing gas such as nitrogen is also flowed into the API interface to assist in nebulizing the analyte/mobile phase matrix. The drying gas, and also the nebulizing gas, can be heated prior to introduction into the API interface. Conventionally, both of these API gases are flowed under constant temperature and flow rate conditions.

In the operation of an LC/MS system, it is important to optimize both the efficiency of the separation accomplished by the LC column so that differing analytes are properly separated within a reasonable run time, and the efficiency of the mass spectrometer so that the mass spectrum produced thereby maximizes the signal-to-noise ratio (S/N) and the resolution of the chromatographic peaks. The process of vaporizing the analyte/mobile phase matrix in the API interface can affect the performance of the mass spectrometer and hence the analytical value of the mass spectrum produced thereby.

Traditionally, a chromatographic separation has entailed isocratic elution in which the mobile phase consists of a single solvent of constant composition. For the afore-mentioned API interface operating according to fixed temperature and flow of the API gases, optimal efficiency of droplet evaporation is only achieved for a single composition of liquid chromatographic solvents. For isocratic separations, these fixed conditions are acceptable in most cases.

It has become increasingly desirable, however, to perform a chromatographic separation that entails gradient elution. In a gradient elution, the mobile phase consists of a multi-solvent system (typically two or three solvents differing significantly in polarity and volatility), and the ratio of the respective solvents in the mobile phase composition is varied continuously or step-wise over time in a programmed or at least predetermined manner. For example, in reversed-phase liquid chromatography, the gradient profile can entail steadily increasing the percentage of an organic solvent in the mobile phase while decreasing that of a less volatile solvent such as water. Gradient elution can significantly improve separation efficiency, and can be employed to change the retention factor of the mobile phase to improve chromatographic resolution of two or more species.

Unfortunately, when gradient elution is performed, the fixed conditions for the API gases result in less than optimal efficiency in the API interface as the mobile phase conditions deviate from the essentially single solvent composition that was used to set up the analysis. As the composition of the mobile phase changes according to the gradient profile, properties such as the surface tension of the droplets, the viscosity of the mobile phase, and the volatility of the mobile phase likewise change. It is believed that prior to the subject matter disclosed herein, there has been no means to adequately compensate for the effects of varying the composition of the mobile phase, particularly at one or the other extreme region of the gradient. As a consequence, the evaporation of droplets and the signals detected by the mass spectrometer have not been optimized for all analytes across the gradient separation. Moreover, there has been an unacceptable opportunity for thermal degradation of a given analyte to occur under gas conditions that are too aggressive for a mobile phase composition associated with that analyte at a particular instance.

In view of the foregoing, it would be advantageous to operate an LC/MS system set up for gradient elution in a manner that optimizes evaporation of the droplets in the API interface in response to the varying mobile phase composition, thereby improving signal detection and reducing the risk of thermal degradation. The subject matter disclosed herein addresses, in whole or in part, these and other problems associated with analytical techniques involving gradient elution.

SUMMARY OF THE INVENTION

A method is provided for optimizing an LC/MS system for gradient elution. According to the method, a temperature profile is determined according to which a gas is to be flowed into an API interface for vaporizing a matrix to be flowed into the API interface. The matrix comprises a mobile phase and a plurality of analytes to be carried in the mobile phase for separation in the column. The mobile phase comprises at least two solvents to be flowed through the column according to a composition gradient profile. The temperature profile varies the temperature of the gas as the composition of the mobile phase varies for optimizing vaporization of the mobile phase along the gradient profile.

In another method for optimizing an LC/MS system for gradient elution, an elution time is determined at which a matrix eluting from an LC column comprises an analyte desired for detection by a mass spectrometer. The matrix comprises a plurality of analytes and a mobile phase to be eluted from a column into an API interface of the mass spectrometer. The mobile phase comprises at least two solvents to be flowed through the column according to a composition gradient profile. Based on the elution time, a flow profile is determined according to which a gas is to be flowed into the API interface. The flow profile varies the gas flow to provide a flow low enough to enable the matrix to enter an evacuated region of the mass spectrometer when the matrix comprises a desired analyte, and to provide a flow high enough to prevent the matrix from entering the evacuated region when the matrix does not comprise a desired analyte.

In yet another method for optimizing an LC/MS system for gradient elution, a first temperature is determined for a gas to be flowed into an API interface for adding heat to the least volatile of the solvents of a mobile phase, and a second temperature is determined for the gas for adding heat to the most volatile of the solvents. The determination of the first and second temperatures is based on a composition gradient profile according to which the mobile phase, comprising at least two solvents of differing volatilities, is to be flowed through an LC column and into the API interface, and based on a flow rate of the mobile phase into the API interface. Based on the first and second temperatures, a varying portion of a temperature profile is determined according to which the gas is to be flowed into the API interface. For a sample to be separated into a plurality of analytes in the column, including first and second analytes, a first elution time and a second elution time are determined. The first elution time is the time at which the first analyte is eluted from the column, and the second elution time is the time at which the last analyte is eluted from the column. Based on the first and second elution times, at least a portion of a flow profile is determined according to which the gas is to be flowed into the API interface generally over a period from the first elution time to the second elution time.

A method is also provided for operating an LC/MS system adapted for gradient elution. According to the method, an eluent is flowed from an LC column into an API interface. The eluent comprises a mobile phase and analytes carried in the mobile phase and separated by the column. The mobile phase comprises at least two solvents, and is flowed through the column according to a gradient profile for varying the composition of the eluent. A gas is flowed into the API interface for interacting with the eluent. The flow of the gas into the API interface is controlled according to a gas parameter profile. The gas parameter profile varies a parameter of the gas, such as temperature and/or flow, in accordance with the varying composition of the eluent.

According to one embodiment, an apparatus is provided for optimizing a chromatographic process for gradient elution. The apparatus comprises an API interface for ionizing a chromatographic eluent of varying composition flowing therein, a gas conduit for flowing a gas into the API interface for interaction with the eluent, and a heating control device for controlling a temperature of the gas flowing through the gas conduit according to a temperature profile. The temperature profile varies the gas temperature based on the varying composition of the eluent.

According to another embodiment, the apparatus comprises a flow control device for controlling the flow of the gas into the API interface according to a flow profile, wherein the flow profile varies the gas flow based on the varying composition of the eluent.

According to yet another embodiment, the apparatus comprises an electronic controller for controlling the heating control device and the flow control device in accordance with the temperature profile and flow profile, respectively.

According to yet another embodiment, the apparatus comprises a computer program product comprising computer-executable instructions embodied in a computer-readable medium for controlling the heating control device and the flow control device in accordance with the temperature profile and flow profile, respectively.

DETAILED DESCRIPTION OF THE INVENTION

Figure 1:
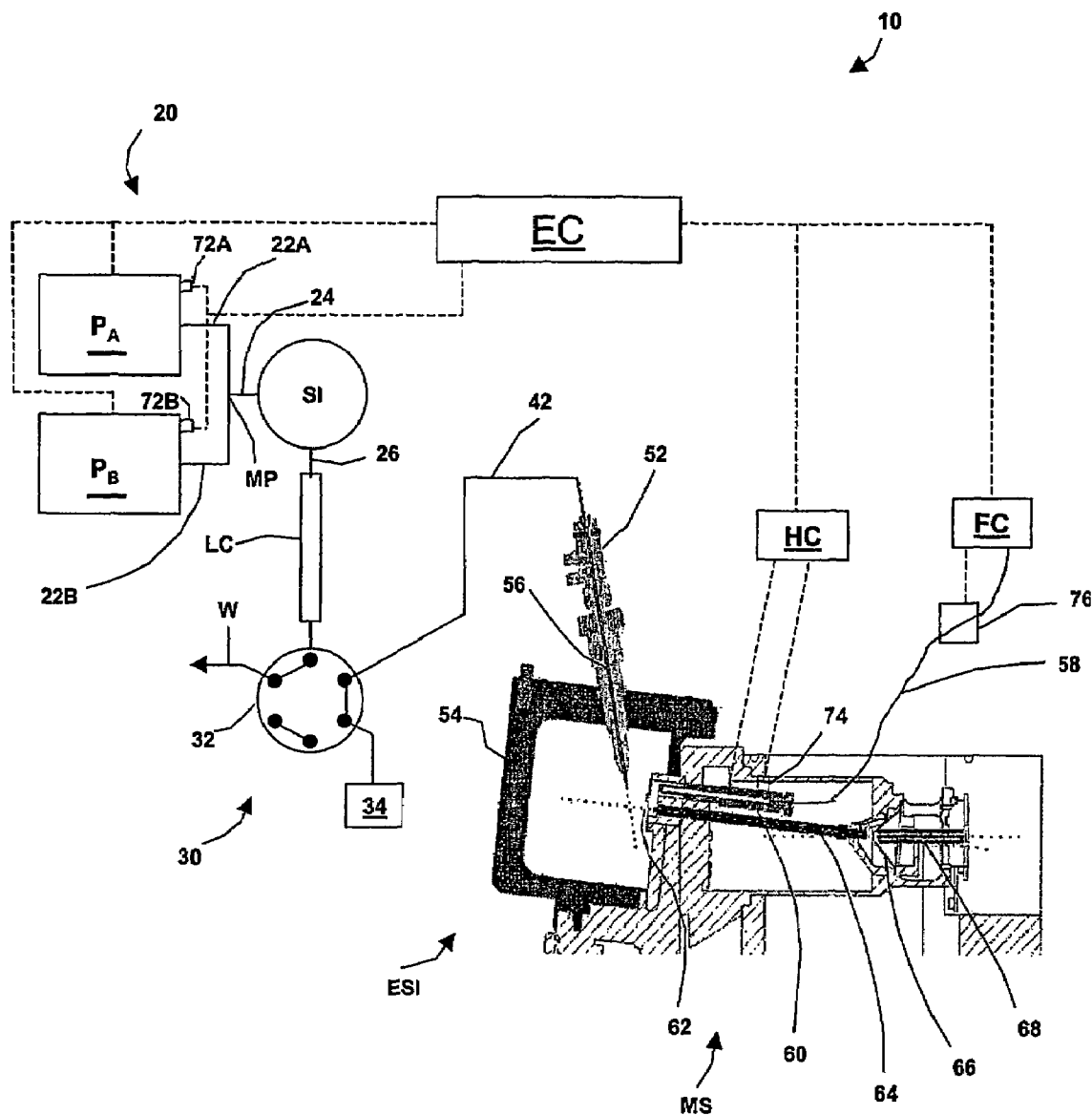
FIG. 1 is a schematic view of an exemplary liquid chromatography/mass spectrometry (LC/MS) system in which programmable temperature and flow profiles for a gas can be implemented in accordance with the subject matter disclosed herein.

Referring now to FIG. 1, an exemplary liquid chromatography/mass spectrometry (LC/MS) system, generally designated 10, is illustrated. LC/MS system 10 includes a solvent/analyte delivery system, generally designated 20, and particularly one suitable for producing a solvent composition gradient profile; a chromatographic separation instrument, which advantageously is a liquid chromatography column or cartridge LC, and particularly a column or cartridge suitable for high-performance liquid chromatography (HPLC); a mass spectrometer, generally designated MS, that includes a suitable API interface such as an electrospray ionization source, generally designated ESI; and a suitable electronic microprocessor or microcontroller EC such as operates in a PC workstation.

Solvent delivery system 20 includes one or more liquid movers such as pumps as needed to establish streams of flowing solvents. In the present example, a first pump $P_A$ and a second pump $P_B$ are provided to establish two initially independent flows of solvents, which typically are of differing compositions and thus differing volatilities. As one example, in the case of reversed-phase liquid chromatography, one solvent has an organic composition such as acetonitrile, methanol, tetrahydrofuran, or the like, and the other solvent has an inorganic composition such as water. An organic solvent is typically more volatile than an inorganic solvent, and thus requires less heat energy to vaporize. Depending on the type of pump design selected, the solvents can be supplied from reservoirs (not shown) either external or internal to first and second pumps $P_A$ and $P_B$.

First and second pumps $P_A$ and $P_B$ can be of any type that can move their respective solvents according to varying, controllable flow rates in order to produce a gradient profile in which the respective compositions of the solvents, after their merging or combination, varies over time. As one example, first and second pumps $P_A$ and $P_B$ can be linear displacement pumps such as syringe-type or reciprocating pumps. As appreciated by persons skilled in the art, a linear displacement pump typically includes a barrel in which the solvent is provided, and a movable boundary such as a piston that is translated through the length of the barrel to push the solvent out therefrom. The piston is typically powered by a suitable motor such as a microstepper motor via a coupling such as a rotating lead screw coupled with a linear stage. The lead screw extends from the motor, and the linear stage is coupled to the piston in a manner that enables the rotary motion of the lead screw to be converted into linear motion of the linear stage and hence the piston.

It will be understood, however, that the embodiments disclosed herein are not limited to the number of solvents, the number of pumps, or the type of pumps employed. In other embodiments, the gradient profile could be established by a solvent proportioning valve placed in-line between solvent reservoirs and a single pump, in which case the pump would pull the solvents from their respective reservoirs through the proportioning valve at variable flow rates controlled by the proportioning valve. Moreover, the mobile phase can include other components or additives, such as certain acids (e.g., formic acid, trifluoroacetic acid (TFA), or the like), as needed for the particular LC procedure being implemented. The selection of the solvents and any other components for the mobile phase can depend on a number of factors, including the type of chromatography being implemented (e.g., ion exchange, ion pair, normal bonded phase, reversed bonded phase, liquid-liquid, size exclusion, or the like), the type of stationary phase being employed, the molecular structures of the analytes to be detected, and so on.

The solvents moved by first and second pumps $P_A$ and $P_B$ flow through respective pump output lines 22A and 22B. To produce a gradient profile among the solvents, the solvents are merged or combined at a merge point MP according to any known technique. FIG. 1 schematically depicts a tee connection to represent merge point MP of the solvent streams after flowing through pump output lines 22A and 22B. Other than a tee connection, any suitable means for merging the solvent streams can be employed, additional examples being a manifold, mixing chamber or mixing valve.

Solvent delivery system 20 includes a sample injector SI downstream from merge point MP for introducing a sample into the mobile phase stream to produce a flowable sample/mobile phase matrix. The sample contains analytes, or components of interest, to be chromatographically separated by column LC and detected by mass spectrometer MS. Any suitable sample injector SI can be employed. As appreciated by persons skilled in the art, one common sample injector SI is a multi-port valve. In one position, the multi-port valve enables a sample loop to be filled with the sample from a manually operated syringe or suitable autosampler, while the mobile phase is flowed through a transfer line 24 from merge point MP to an input line 26 to column LC. In another position, the multi-port valve redirects flow from transfer line 24 to flush the sample in the sample loop into input line 26 for transport with the mobile phase into column LC.

It will be understood that solvent delivery system 20 can comprise any other additional components deemed necessary or desirable for delivering the mobile phase and sample to column LC. Examples include degassing, filtering, and pulse dampening components.

Column LC can be any commercially available column. Column LC commonly is packed with a durable support for a stationary phase with which analytes of the sample carried with the mobile phase interact so as to be discriminated according to differing retention times. The most common types of supports for stationary phase components are solid, particularly in the case of partition chromatography. Thus, a typical durable support is a packing of beads or other particles held within column LC. The packing material commonly comprises particles having an inorganic ceramic composition, such as silica or alumina, but could also be organic polymeric particles such as polystyrene-divinyl benzene. In the case of reversed-phase chromatography, the stationary phase is typically formed from silica beads to which alkyl chains, such as octyldecyl ($C_{18}$), are bonded (e.g., octyldecylsilane or ODS).

Also illustrated in FIG. 1 is a mobile phase diverting system, generally designated 30, disposed in-line between column LC and electrospray ionization source ESI. Mobile phase diverting system 30 typically includes a diverter valve 32, such as a multi-port valve, as well as an auxiliary pump 34 and a waste line W. As appreciated by persons skilled in the art, mobile phase diverting system 30 is often employed to divert the eluent from column LC away from mass spectrometer MS during stages at which the eluent is not expected to contain components having significant analytical value. For instance, prior to any significant retention of analytes on the stationary phase in column LC, the eluent is essentially the mobile phase contained in the void volume of column LC. In addition, after a separation procedure has been performed, rinse solvents are often pumped through column LC to wash column LC in preparation for the next chromatography run. Detection of these portions of the eluent from column LC is avoided by diverting the eluent to waste W during such stages. As will become evident from the following description, the method disclosed herein, and particularly its establishment of a flow profile for an API gas introduced into electrospray ionization source ESI, eliminates the need for providing mobile phase diverting system 30 as part of LC/MS system 10.

The eluent from column LC, i.e., an analyte/mobile phase matrix, is flowed from column LC to electrospray ionization source ESI over a transfer line 42. Electrospray ionization source ESI includes an electrospray device 52 extending into a chamber 54 maintained at atmospheric or substantially atmospheric pressure. Electrospray device 52 includes a metal or metallized capillary 56 fluidly communicating with transfer line 42. Capillary 56 is maintained at a voltage level with respect to another conductive component, such as an a spray shield, with the result that the analyte/mobile phase matrix is discharged from the tip of capillary 56 into chamber 54 in the form of an electrospray. To assist in desolvating the charged droplets, an inert drying gas such as nitrogen is flowed into chamber 54 via a gas line 58 from suitable gas supply and delivery system (not shown). The drying gas is heated prior to being introduced into chamber 54, such as by flowing the drying gas through an in-line heater 60. As described in more detail below, the drying gas is controlled in accordance with a time-varying temperature profile and/or a time-varying volumetric flow profile.

It will be understood that in many cases, depending on the flow rate of the matrix through transfer line 42 and/or the internal volume of transfer line 42, the period of time over which the matrix flows through transfer line 42 can be negligible. Accordingly, for the purposes of the present disclosure, the time at which the matrix is eluted from the outlet of column LC can be considered the same or approximately the same as the time at which the matrix is flowed into chamber 54 from electrospray device 52.

As appreciated by persons skilled in the art, electrospray ionization source ESI can also include means (not shown) for flowing an inert nebulizing gas such as nitrogen into chamber 54 to enhance droplet formation, particularly for flow rates of approximately 0.02 ml/min or greater. As an example, an additional conduit can be annularly disposed about capillary 56 of electrospray device 52 for directing the nebulizing gas through the annular space defined between this additional conduit and capillary 56. In this configuration, often termed pneumatically-assisted electrospray ionization, both the nebulizing gas and the matrix enter chamber 54 from the tip of electrospray device 52. Examples of the use of nebulizing gas in electrospray ionization are disclosed in commonly assigned U.S. Pat. No. 6,207,955 to Wells et al., the content of which is incorporated herein in its entirety. In accordance with some embodiments of the subject matter disclosed herein, electrospray ionization source ESI includes means for flowing a nebulizing gas into chamber 54. In accordance with additional embodiments, the nebulizing gas is heated to provide an additional means for adding heat to the matrix to optimize vaporization.

An electric field gradient is established within chamber 54 by known means to attract the charged analyte-containing droplets into an inlet 62 of mass spectrometer MS. Typically, the ions travel through a capillary 64 in a first vacuum stage of mass spectrometer MS. The ions then pass through a skimmer plate 66 into a second vacuum stage of mass spectrometer MS, which can include a multi-pole structure or other suitable ion guide or focusing device 68, and are detected in order to generate a mass spectrum of the sample for analysis.

It will be understood that FIG. 1 provides one example of certain components of mass spectrometer MS, and that many other known designs of mass spectrometers could alternatively be employed.

In accordance with the subject matter disclosed herein, LC/MS system 10 further includes a heater control device HC and a flow control device FC for controlling the input of the drying gas according to a temperature profile and a volumetric flow profile, respectively. Heater control device HC electrically communicates with heater 60, and includes any hardware and/or circuitry suitable for variably controlling the heat transfer from heater 60 to the drying gas, and hence controlling the temperature of the drying gas, according to a predetermined or preprogrammed temperature profile. Flow control device FC communicates with gas line 58, and includes any hardware and/or circuitry suitable for variably controlling the volumetric flow rate of the drying gas into chamber 54 according to a predetermined or preprogrammed flow profile. Any suitable flow control device FC can be employed, including one that controls the flow by controlling the pressure in gas line 58 (i.e., a pressure control device).

In advantageous embodiments, electronic controller EC communicates with solvent delivery system 20 (e.g., with first and second pumps $P_A$ and $P_B$), heater control device HC, and/or flow control device FC to electronically control these components. Thus, electronic controller EC can be employed to control the gradient profile, the temperature profile, and/or the flow profile during the operation of LC/MS system 10.

According to one aspect, a user of LC/MS system 10 first determines the appropriate gradient profile, temperature profile, and flow profile, and inputs data into electronic controller EC as necessary to program the profiles into electronic controller EC. As appreciated by persons skilled in the art, a suitable computer program can be written to provide the interface between the user and electronic controller EC for the purpose of programming electronic controller EC. According to one embodiment, the apparatus disclosed herein comprises a computer program product including computer-executable instructions embodied in a computer-readable medium for implementing the temperature profile and flow profile, such as by enabling electronic controller EC to control heater control device HC and flow control device FC.

In the operation of LC/MS system 10, electronic controller EC executes these programs by downloading appropriate signals to solvent delivery system 20, heater control device HC, and/or flow control device FC so as to implement the gradient profile, temperature profile, and/or flow profile, respectively. To ensure that these profiles are properly maintained during operation of LC/MS system 10, suitable sensors or transducers can be provided to generate feedback signals for electronic controller EC, heater control device HC, and/or flow control device FC so that adjustments can be made in response to detected deviations from the correct profiles. For example, the sensors or transducers can include encoders 72A and 72B positioned at first and second pumps $P_A$ and $P_B$, respectively, as are typically provided with linear displacements pumps, a thermocouple 74 appropriately positioned at heater 60, and a pressure transducer or other flow measurement device 76 appropriately positioned in-line with gas line 58.

Figure 2:
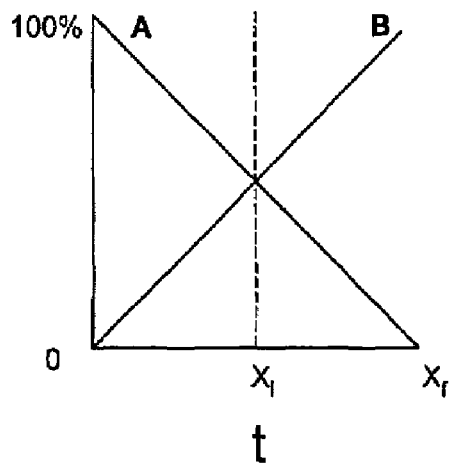
FIG. 2 is a plot of an exemplary mobile phase composition gradient profile according to which the LC/MS system can operate.
Figure 3:
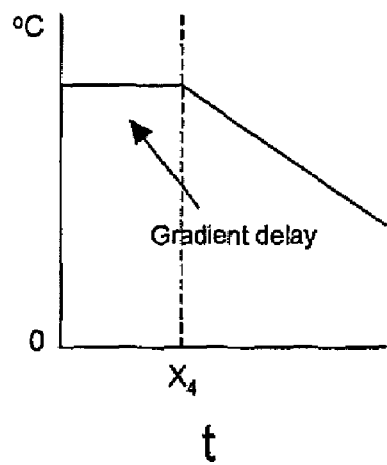
FIG. 3 is a plot of an exemplary gas temperature profile according to which the LC/MS system can operate.

A method for optimizing LC/MS system 10 for gradient elution will now be described with continuing reference to FIG. 1 and the profiles illustrated by way of example in FIGS. 2-4. In accordance with the method, the gradient profile is first determined for a given mobile phase, stationary phase, and analyte-containing sample. FIG. 2 is an example of a gradient profile for a mobile phase that comprises a binary solvent system. More specifically, FIG. 2 is a plot of mobile phase composition as a function of time constructed from the flow profiles for two solvents, solvent A and solvent B. In the present example, solvent A is an inorganic solvent such as water, and solvent B is an organic solvent and hence is more volatile than solvent A. Assuming the mobile phase includes no other components prior to injection of a sample, total composition of the mobile phase at any point in time is 100%. In the present example, at time t=0, the composition of solvent A in the mobile phase is 100% and the composition of solvent B in the mobile phase is 0%. At the end of the gradient elution through column LC ($t=x_f$), the composition of solvent A is 0% and the composition of solvent B is 100%. Thus, the exemplary gradient profile is characterized by the composition of solvent A decreasing while the composition of solvent B is increased, such that the volatility of the mobile phase increases over time. At some intermediate time ($t=x_i$) between the initial and final times, the flow curve for solvent A intersects the flow curve for solvent B, at which point the mobile phase has 50% solvent A/50% solvent B composition. The flow curves for the solvents can be linear as depicted in FIG. 2, non-linear (e.g., exponential), or stepped, or can include combinations of linear, non-linear, and/or stepped portions.

Prior to performing a chromatographic separation technique, the user of LC/MS system 10 empirically determines a gradient profile such as shown in FIG. 2. The determination of the gradient profile for a given sample and separation technique is well known in the art, and thus does not require a detailed description herein. As an example, according to one technique for a binary mobile phase comprising an inorganic solvent such as water and an organic solvent, the user determines how weak the initial composition of the organic solvent in the mobile phase needs to be in order to realize adequate retention of the first analyte of the sample. If the composition is initially too strong, the first analyte will either be unretained or barely retained and thus will elute from column LC too close to the void volume. Then, the user determines how quickly the compositional gradient needs to be increased so that the last analyte of the sample is eluted at an acceptable elution time. It can be seen that the resulting gradient profile provides information regarding the extremes of volatility in the gradient and the composition of the mobile phase at any instant of time during elution.

Once the gradient profile has been determined, the temperature profile for the drying gas is determined. FIG. 3 is an example of a temperature profile. More specifically, FIG. 3 is a plot of drying gas temperature as a function of time. In the present example, in advantageous embodiments, the temperature profile includes a constant portion between $t=0$ and $t=x_4$, as well as a varying or sloped portion subsequent to $t=x_4$. In advantageous embodiments, the delay volume of LC/MS system 10 is first measured to determine the gradient delay time. Generally, the delay volume or gradient delay time represents the time required for a change in the gradient composition—i.e., the mobile phase at some point along the gradient—to reach the API interface of mass spectrometer MS. For the specific example of LC/MS system 10 illustrated in FIG. 1, where the gradient is effected by varying the respective flow rates of the individual solvents prior to mixing, the delay volume corresponds to time required for the mobile phase to travel from merge point MP or thereabouts to the tip of electrospray capillary 56 in chamber 54. The horizontal (constant) portion of the temperature curve ($t=0$ to $t=x_4$) generally represents the delay volume for the compositional gradient. The point on the curve where the horizontal portion meets the sloped portion (corresponding to $t=x_4$) generally represents the point in time where the mobile phase, as composed at the beginning of the gradient profile, has reached electrospray ionization source ESI in the exemplary system illustrated in FIG. 1.

During the delay time, the mobile phase is flowed through electrospray capillary 56 into chamber 54 to keep capillary 56 wet and prevent salt deposits. The portion of the mobile phase flowing into chamber 54 during the delay time has not yet been subjected to the gradient profile, and the first analyte has not yet been eluted from column LC. Thus, the composition and volatility of the mobile phase do not appreciably change during the delay time. Moreover, in the present example, the volatility of the mobile phase in the delay volume is relatively low and thus requires a relative large amount of heat energy for vaporization. Accordingly, the temperature of the drying gas is maintained at a relatively high constant temperature to optimize vaporization of the mobile phase during the delay time. In addition, because the eluent from column LC during the delay volume contains no analytes of interest, optimizing vaporization the mobile phase during this time likewise facilities the ability of drying gas to sweep this portion of the mobile phase away from inlet 62 of mass spectrometer MS, thereby preventing the mobile phase from being detected by mass spectrometer MS and adversely affecting the mass spectrum generated thereby. Also, the drying gas prevents the mobile phase from fouling the evacuated regions of mass spectrometer MS during the delay time.

In addition to determining the delay volume, the temperature profile for the drying gas is determined during the time the gradient elution is effective to change the volatility of the analyte/mobile phase matrix as it is discharged from electrospray device 52. For the gradient profile given by way of example in FIG. 1, volatility increases from a minimum value to a maximum value, and thus the amount of heating power required to vaporize the mobile phase changes as the composition of the mobile phase changes. Accordingly, after the delay volume has passed through LC/MS system 10, the amount of heat energy needed to vaporize the droplets of the electrospray in chamber 54 begins to lessen over time, particularly in the case of thermally labile components in the droplets of the analyte/mobile phase matrix. Thus, the temperature of the drying gas is adjusted as a function of time to optimally match the drying gas temperature with the composition of the mobile phase during the course of the compositional gradient.

The variable portion of the temperature profile is determined from the elution characteristics of the mobile phase. More specifically, for a given flow rate of the analyte/mobile phase matrix into chamber 54, optimal drying gas temperatures corresponding to the least volatile mobile phase composition and the most volatile mobile phase composition are determined, respectively. The variable portion of the temperature profile between these two extremes (i.e., the highest and lowest temperatures) is then determined by any suitable technique. For example, if the gradient profile is linear, the optimal temperature profile can be empirically approximated by linear interpolation between the two extremes as shown in FIG. 3. In the present example, the least volatile mobile phase composition occurs at the beginning of the gradient profile and the most volatile mobile phase composition occurs at the end of the gradient profile. It will be understood, however, that the subject matter disclosed herein is not limited to this type of gradient profile. For instance, the temperature profile can be non-linear. Moreover, the gradient profile could be stepped (i.e., have one or more slope changes), in which case it might be desirable to determine the optimal drying gas temperature or temperatures for one or more intermediate conditions.

Figure 4:
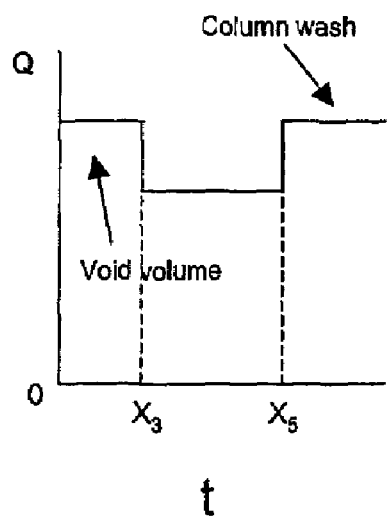
FIG. 4 is a plot of an exemplary gas flow profile according to which the LC/MS system can operate.

FIG. 4 is an example of a volumetric flow profile for the drying gas. More specifically, FIG. 4 is a plot of drying gas flow rate as a function of time. It will be understood, however, that in the case where flow control device FC operates by adjusting the pressure in gas line 58, FIG. 4 can equivalently represent a pressure profile; thus, the term "flow profile" can also be understood as meaning "pressure profile" in such a case. In one embodiment, the determination of the flow profile is based on an elution time at which the matrix eluting from column LC comprises an analyte that is desired to be ionized and transported into mass spectrometer MS via inlet 62 for detection. In advantageous embodiments, the flow profile takes into account the elution characteristics of LC/MS system 10 during the period of time just before the first analyte is eluted from column LC, the period of time after the first analyte has been eluted up until the time that the last analyte has been eluted, and the period of time after the last analyte has been eluted.

During the period of time before the first analyte is eluted, the eluent comprises the mobile phase in the void volume and possibly poorly retained, highly concentrated compounds that elute during or after the void volume. The composition of this portion of the eluent typically has no analytical value, and thus it is desirable to prevent this portion from entering mass spectrometer MS. Accordingly, the first portion of the exemplary flow profile depicted in FIG. 4 corresponds to a relatively high volumetric flow rate for the drying gas sufficient to blow the eluent away from inlet 62. It thus can be seen that the implementation of the flow profile can eliminate the need for mobile phase diverting system 30 and its attendant cost and maintenance requirements. Moreover, because the drying gas is heated as previously described, the increased flow rate during this period enables an increased amount of heat energy to be transferred to the eluent, thereby further optimizing vaporization of the eluent and facilitating its diversion away from inlet 62.

As appreciated by persons skilled in the art, as the sample and mobile phase flow through column LC, the analytes of the sample are separated according their retention times between the mobile phase and the stationary phase. Typically, the differing analytes are eluted with the mobile phase from column LC in sequential bands or zones, and the resulting analyte/mobile phase matrix enters electrospray device 52 and is discharged into chamber 54 from electrospray capillary 56 in the form of electrospray. In accordance with the method disclosed herein, the user determines the time at which the first analyte is eluted from column LC and time at which the last analyte is eluted from column LC. During this period of time, highly charged analyte-containing droplets of a size useful for successful processing by mass spectrometer MS travel through chamber 54 toward inlet 62 to mass spectrometer MS under the influence of an electric field. In addition, some droplets may be too large to be sufficiently desolvated upon entering inlet 62. These large droplets may give rise to large spikes in the response of the mass spectrum and/or carry components that rapidly contaminate the first and second stages of mass spectrometer MS. During this period, the flow rate of the drying gas should be high enough to desolvate the desired smaller droplets and blow away the undesired larger droplets, yet low enough so as not to blow away the smaller droplets. As illustrated in FIG. 4, the flow rate during this period of time is lower in comparison to the previous period of time prior to elution of the first analyte.

Typically, it is desirable to wash column LC and associated fluid lines, valves and the like in LC/MS system 10 after a chromatographic run to eliminate any residual matrix and other contaminates. In some embodiments, the washing step is accomplished by flowing a rinsing solvent through column LC and electrospray device 52. As illustrated in FIG. 4, the flow rate of the drying gas during this period of time can be increased again to divert the rinse solvent away from inlet 62.

It will be understood that while the resulting flow profile shown in FIG. 4 by way of example is a stepped profile, the transitions between higher and lower flow rates can be sloped, either linearly or non-linearly as dictated empirically by the user. Moreover, depending on such factors as the sample, the solvents included in the mobile phase, and the type of gradient profile, there may be one or more intermediate times between elution of the first and last analytes at which a large component or components having little or no analytical value can be expected to be discharged into electrospray ionization source ESI. Hence, it will be understood that the method disclosed herein encompasses intermediate times during which the drying gas flow is increased enough to prevent such undesirable components from entering inlet 62.

As described previously, once the user of LC/MS system 10 has determined the appropriate gradient profile, temperature profile, and flow profile, the user can program the profiles into electronic controller EC for controlling solvent delivery system 20, heater control device HC, and flow control FC device during the chromatographic run. The programs defining the profiles can be executed by hardware, firmware, or software. In the case of software, the user can input data for reading by the software as needed to define the profiles desired by the user, and the software can include the instructions necessary for carrying out the profiles, such as by causing electronic controller EC (e.g., a computer) to send signals to solvent delivery system 20, heater control device HC, and flow control FC device as appropriate for implementing the instructions. In other embodiments, heater control device HC, and flow control FC device can be of the directly programmable type with erasable memory, enabling the user to directly program these control devices.

It will be understood that in cases where the API interface such as electrospray ionization source ESI is of the type that provides a flow of nebulizing gas into chamber 54, the subject matter described thus far can be applied to the nebulizing gas and associated components in addition to, or instead of, the drying gas. That is, the flow nebulizing gas can be controlled according to the temperature and/or flow profiles for interaction with the matrix in a manner generally analogous to that described previously with regard to the drying gas. In the case where both the drying gas and the nebulizing gas are controlled, the respective temperature and/or flow profiles for each gas are determined by taking into account the combined effects of the gases in terms of the amounts of heat energy added by each gas, the flow rates of each gas, and any other relevant thermodynamic and fluid dynamic factors, particularly so as not to impair the normal operation and functions of the API interface in preparing ions for processing by mass spectrometer MS.

The method and apparatus disclosed herein have been described thus far in the context of employing electrospray ionization source ESI as the API interface. Nonetheless, it can be appreciated by persons skilled in the art that an APCI source could also be employed instead of electrospray ionization source ESI to yield similar advantages although, as a general matter, an APCI source is not typically recommended for use with thermally labile or high-molecular-weight compounds. The basic design and operating principles of an APCI source is well known and thus need not be described in detail herein. Briefly, in an APCI source, the capillary employed to transport the eluent into the interface does not include an electrospray device. Instead, the capillary conducts the eluent into a vaporizing chamber. The vaporizing chamber typically is a tube constructed from, or including as its inside surface, an inert material such as quartz. The capillary is surrounded by an annular tube that carries nebulizing gas into the vaporizing chamber with the eluent, thereby nebulizing the eluent as it enters the vaporizing chamber. The vaporizing chamber vaporizes the nebulized eluent as it travels along the axial length of its interior. For this purpose, the wall of the vaporizing chamber is heated by a suitable heater device, and/or an auxiliary drying (or vaporizing) gas can also be flowed into the vaporizing chamber. The vaporized eluent then flows from the vaporizing chamber into an ionizing chamber into which an electrode such as a corona needle extends. This electrode is typically positioned similar to electrospray device 52 illustrated in FIG. 1 herein, and it will be noted that some commercially available mass spectrometers are adapted for easy adjustment between ESI and APCI modes. The electrode strikes a corona discharge with another conductive surface to provide the energy for ionizing the eluent, and the resulting ions enter mass spectrometer MS via inlet 62. An example of an APCI interface is provided in commonly assigned U.S. patent application Ser. No. 10/115,684, the content of which is incorporated herein in its entirety. In the context of the subject matter presently disclosed herein, the temperature and/or flow profiles could be used to control the drying gas and/or the auxiliary vaporizing gas as it flows into the APCI interface.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A method for optimizing an LC/MS apparatus comprising an API interface into which a matrix is to be flowed according to a composition gradient profile, the method comprising:
   (a) determining a temperature profile according to which a gas is to be flowed into the API interface, the matrix comprising at least a first solvent having a first composition and a second solvent having a second composition different from the first composition, wherein the temperature profile varies the temperature of the gas as the composition of the matrix varies along the gradient profile for optimizing vaporization of the matrix, and determining the temperature profile comprises determining a first temperature of the gas for adding heat to the first solvent to evaporate the first solvent and a second temperature of the gas for adding heat to the second solvent to evaporate the second solvent;
   (b) determining a flow profile according to which the gas is to be flowed into the API interface;
   (c) programming an electronic processor-based device to control the flow of the gas into the API interface according to the temperature profile and the flow profile; and
   (d) flowing the gas into the API interface for interacting with the matrix.

2. The method according to claim 1, wherein the first solvent is the least volatile of the solvents flowing into the API interface, and the second solvent is the most volatile of the solvents flowing into the API interface.

3. The method according to claim 1, wherein determining the temperature profile comprises determining a gradient delay time for the LC/MS system.

4. The method according to claim 3, wherein determining the gradient delay time comprises measuring a period of time required for a gradient composition change in the matrix to reach the API interface.

5. The method according to claim 3, wherein the temperature profile comprises a portion corresponding to the gradient delay time, and the portion has a substantially constant temperature value.

6. The method according to claim 1, wherein determining the flow profile comprises determining a first elution time at which a first analyte is to be eluted from an LC column into the API interface.

7. The method according to claim 6, wherein determining the flow profile comprises determining a second elution time at which a last analyte is to be elated from the column into the API interface, wherein at least a portion of the flow profile generally corresponds to a period from the first elution time to the second elution time.

8. The method according to claim 7, comprising determining an initial elution period during which the mobile phase is flowed through the column generally up to the first elution time, and determining another portion of the flow profile based on the initial elution period.

9. The method according to claim 8, wherein the portion of the flow profile corresponding to the initial flow period has a higher flow value than the portion of the flow profile from the first elution time to the second elution time.

10. The method according to claim 7, comprising determining an additional portion of the flow profile subsequent to the second elution time during which a rinse solvent is flowed through the column and into the API interface for washing the column.

11. The method according to claim 1, further comprising controlling the flow of the gas into the API interface according to the temperature profile by controlling a heating device disposed in thermal communication with the gas.

12. An apparatus for optimizing an LC/MS process for gradient elution, comprising:
    (a) an API interface for ionizing a chromatographic eluent flowing therein, the eluent comprising a first solvent having a first composition and a second solvent having a second composition different from the first composition, wherein the composition of the eluent varies over time;
    (b) a gas conduit for flowing a gas into the API interface for interaction with the eluent;
    (c) a heating control device for controlling a temperature of the gas flowing through the gas conduit according to a programmed temperature profile, wherein the temperature profile varies the gas temperature based on the varying composition of the eluent, and the temperature profile is programmed based on determining a first temperature of the gas for adding heat to the first solvent to evaporate the first solvent and a second temperature of the gas for adding heat to the second solvent to evaporate the second solvent;
    (d) a flow control device for controlling the flow of the gas into the API interface; and
    (e) an electronic processor-based device configured for controlling the heating control device and the flow control device in accordance with the temperature profile and a flow profile, respectively.

13. The apparatus according to claim 12, wherein the electronic processor-based device is configured to execute a computer program product including computer-executable instructions embodied in a computer-readable medium for controlling the heating control device and the flow control device in accordance with the temperature profile and flow profile, respectively.

* * * * *